US009976987B2

(12) United States Patent
Freer et al.

(10) Patent No.: US 9,976,987 B2
(45) Date of Patent: May 22, 2018

(54) SYSTEMS FOR TRACKING CORROSION WITHIN ENCLOSURES USING SACRIFICIAL LOOP TARGETS

(71) Applicants: Benjamin Avery Freer, Syracuse, NY (US); Jesse Wade Taylor, Baldwinsville, NY (US)

(72) Inventors: Benjamin Avery Freer, Syracuse, NY (US); Jesse Wade Taylor, Baldwinsville, NY (US)

(73) Assignee: Cooper Technologies Company, Houston, TX (US)

( * ) Notice: Subject to any disclaimer, the term of this patent is extended or adjusted under 35 U.S.C. 154(b) by 0 days. days.

(21) Appl. No.: 15/350,731

(22) Filed: Nov. 14, 2016

(65) Prior Publication Data
US 2017/0160237 A1 Jun. 8, 2017

Related U.S. Application Data

(60) Provisional application No. 62/264,483, filed on Dec. 8, 2015.

(51) Int. Cl.
*G01N 27/90* (2006.01)
*G01N 17/00* (2006.01)

(52) U.S. Cl.
CPC ..... *G01N 27/9073* (2013.01); *G01N 27/9006* (2013.01); *G01N 17/00* (2013.01)

(58) Field of Classification Search
CPC . G01N 27/9073; G01N 17/00; G01N 27/9006
USPC ................................ 324/228–243
See application file for complete search history.

(56) References Cited

U.S. PATENT DOCUMENTS

| 4,593,245 | A  | * | 6/1986  | Viertl ................. G01N 27/9033 324/238 |
| 6,636,037 | B1 |   | 10/2003 | Ou-Yang |
| 7,095,224 | B2 |   | 8/2006  | Goldfine et al. |
| 7,560,920 | B1 |   | 7/2009  | Ouyang et al. |
| 2005/0068026 | A1 | * | 3/2005 | May ................... G01N 27/9046 324/228 |
| 2012/0019236 | A1 | * | 1/2012 | Tiernan .............. G01N 27/9033 324/234 |

FOREIGN PATENT DOCUMENTS

WO    2015159226    10/2015

OTHER PUBLICATIONS

A. Semenova., International Search Report and Written Opinion of the International Searching Authority for PCT/US2016/061825, completion date Feb. 10, 2017, dated Mar. 30, 2017, 7 pages, Federal Institute of Industrial Property, Moscow, Russia.

* cited by examiner

*Primary Examiner* — Jay Patidar
(74) *Attorney, Agent, or Firm* — King & Spalding LLP

(57) ABSTRACT

A corrosion tracking system within an enclosure can include an electrical circuit through which a first current flows, where the first current creates a magnetic field. The system can also include a target component disposed proximate to the electrical circuit, where the magnetic field induces a number of second currents to flow within the target component. The system can further include a sensor that measures the plurality of second currents flowing within the target component to generate a plurality of measurements. The measurements can indicate whether the target component is experiencing corrosion.

19 Claims, 8 Drawing Sheets

SYSTEMS FOR TRACKING CORROSION WITHIN ENCLOSURES USING SACRIFICIAL LOOP TARGETS

CROSS-REFERENCE TO RELATED APPLICATIONS

This application claims priority under 35 U.S.C. § 119 to U.S. Provisional Patent Application Ser. No. 62/264,483, titled "Eddy Current Corrosion Sensor" and filed on Dec. 8, 2015, the entire contents of which are hereby incorporated herein by reference.

TECHNICAL FIELD

The present disclosure relates generally to detecting corrosion, and more particularly to systems, methods, and devices for eddy current corrosion sensors.

BACKGROUND

Electrical enclosures are used in a number of applications and have a number of different sizes and configurations. Such electrical enclosures have one or more electrical devices and/or mechanical devices disposed therein. One or more of the mechanical devices can operate based on a change of state of an electrical device. Sometimes, the environments in which these electrical enclosures are located are subject to one or more environmental conditions (e.g., high temperatures, high humidity, moisture) that can be present inside an electrical enclosure. When this occurs, damage can occur to the electrical devices, causing the electrical devices to fail and creating a potential safety concern. Similarly, if a mechanical device corrodes or otherwise fails because of unfavorable environmental conditions within the electrical enclosure, the mechanical device may fail to operate when an electrical device changes state, which can also create a safety concern. In addition, the interior surfaces of the electrical enclosure can become corroded or otherwise damaged. Typically, electrical enclosures are opened on a very infrequent basis, and so a user is often unaware of an adverse condition within the electrical enclosure that can affect the electrical and/or mechanical devices located within the electrical enclosure.

SUMMARY

In general, in one aspect, the disclosure relates to a corrosion tracking system within an enclosure. The system can include an electrical circuit through which a first current flows, where the first current creates a magnetic field. The system can also include a target component disposed proximate to the electrical circuit, where the magnetic field induces a number of second currents to flow within the target component. The system can further include a sensor that measures the second currents flowing within the target component to generate a number of measurements. The measurements can indicate whether the target component is experiencing corrosion.

In another aspect, the disclosure can generally relate to an electrical enclosure. The electrical enclosure can include at least one wall that forms a cavity. The electrical enclosure can also include a first device disposed within the cavity, where the first device includes a first material subject to first corrosion. The electrical enclosure can further include a first corrosion tracking system disposed within the cavity adjacent to the first device. The first corrosion tracking system can include a first electrical circuit through which a first current flows, where the first current creates a first magnetic field. The first corrosion tracking system can also include a first target component disposed proximate to the first electrical circuit, where the first magnetic field induces a number of second currents to flow within the first target component. The first corrosion tracking system can further include a first sensor that measures the second currents flowing within the first target component to generate a number of first measurements. The first measurements can indicate whether the first target component is experiencing second corrosion. The second corrosion of the first target component can indicate a level of the first corrosion in the first device.

These and other aspects, objects, features, and embodiments will be apparent from the following description and the appended claims.

BRIEF DESCRIPTION OF THE DRAWINGS

The drawings illustrate only example embodiments and are therefore not to be considered limiting in scope, as the example embodiments may admit to other equally effective embodiments. The elements and features shown in the drawings are not necessarily to scale, emphasis instead being placed upon clearly illustrating the principles of the example embodiments. Additionally, certain dimensions or positionings may be exaggerated to help visually convey such principles. In the drawings, reference numerals designate like or corresponding, but not necessarily identical, elements.

DETAILED DESCRIPTION

Figure 1:
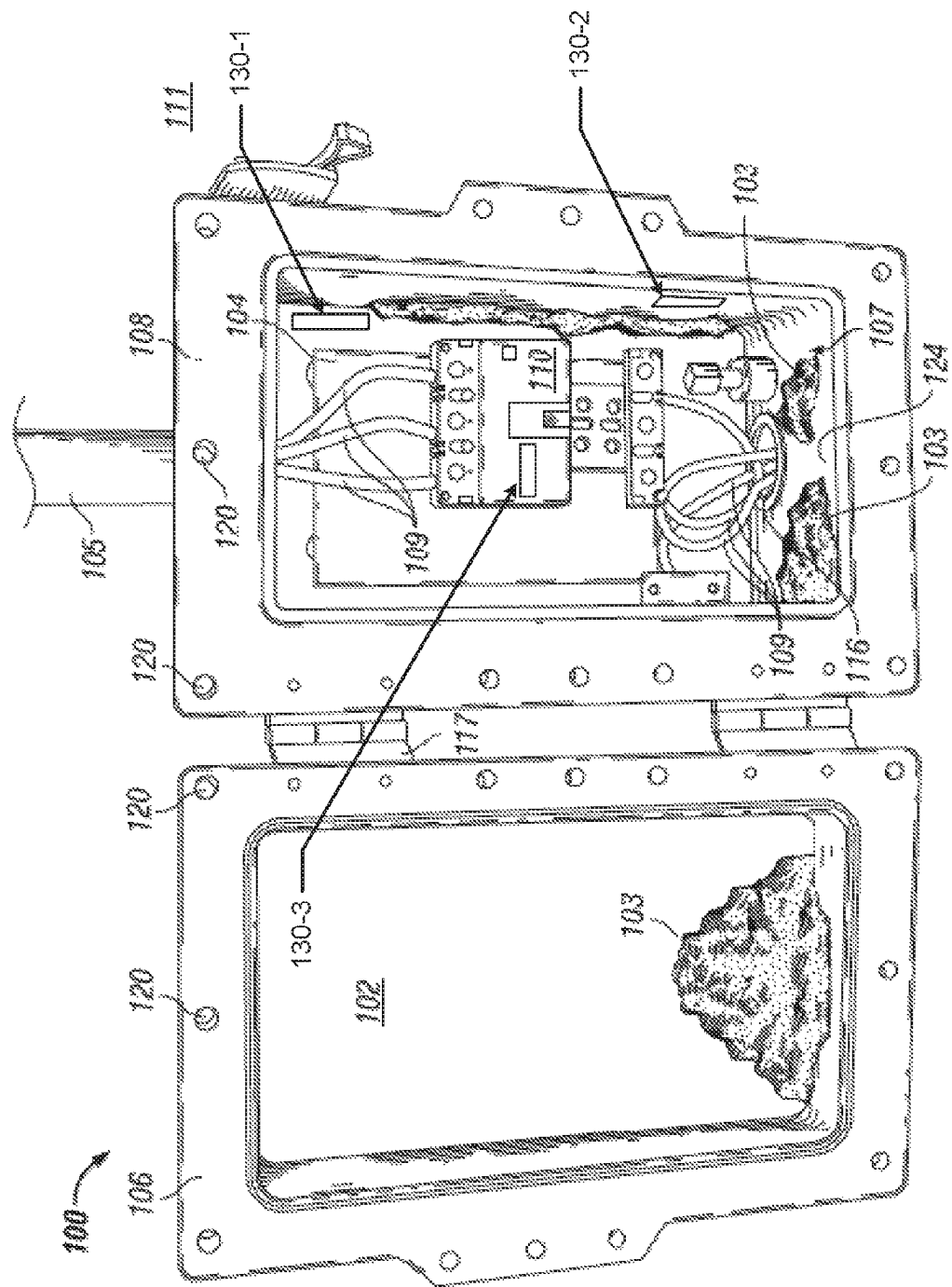
FIG. 1 shows a front view of an enclosure in accordance with certain example embodiments.

In general, example embodiments provide systems, methods, and devices for eddy current corrosion sensors, also called corrosion tracking systems herein. Example eddy current corrosion sensors can be used in any of a number of applications, including but not limited to electrical enclosures (e.g., junction boxes, conduit, control panels, motor housings), electrical devices (e.g., light fixture, switch), and mechanical devices (relay contact, contactor). Further, example eddy current corrosion sensors can be used in one or more of any of a number of environments, including but not limited to hazardous (e.g., explosive) environments, indoors, outdoors, cold temperatures, hot temperatures, high humidity, marine environments, and low oxygen environments. A user may be any person that interacts, directly or indirectly, with electrical and/or mechanical devices. Examples of a user may include, but are not limited to, an engineer, an electrician, an instrumentation and controls technician, a mechanic, an operator, a consultant, a contractor, and a manufacturer's representative.

In the foregoing figures showing example embodiments of eddy current corrosion sensors, one or more of the components shown may be omitted, repeated, and/or substituted. Accordingly, example embodiments of eddy current corrosion sensors should not be considered limited to the specific arrangements of components shown in any of the figures. For example, features shown in one or more figures or described with respect to one embodiment can be applied to another embodiment associated with a different figure or description.

In some cases, example eddy current corrosion sensors can be used in any of a number of enclosures. Examples of such enclosures can include electrical enclosures and mechanical enclosures. As defined herein a mechanical enclosure is any type of cabinet or housing inside of which is disposed one or more mechanical devices. A mechanical enclosure can also include one or more electrical devices. Examples of a mechanical enclosure can include, but are not limited to, a tool box, a gang box, a storage crate, and a shipping container.

Also, as defined herein, an electrical enclosure is any type of cabinet or housing inside of which is disposed one or more electrical devices. An electrical enclosure can also include one or more mechanical devices. Such electrical and/or mechanical devices can include, but are not limited to, variable frequency drives (VFDs), controllers, relays (e.g., solid state, electro-mechanical), contactors, breakers, switches, transformers, inverters, converters, fuses, electrical cables, thermo-electric coolers (TECs), heating elements, air moving devices (e.g., fans, blowers), terminal blocks, wire nuts, and electrical conductors. In some cases, an electrical and/or mechanical device can generate heat when operating. Electrical devices can also include mechanical components and/or mechanical devices that are controlled by an electrical device. Examples of an electrical enclosure can include, but are not limited to, an electrical connector, a junction box, a motor control center, a breaker cabinet, an electrical housing, a conduit, a control panel, an electrical receptacle, a lighting panel, a lighting device, a relay cabinet, an indicating panel, and a control cabinet.

In certain example embodiments, enclosures in which example eddy current corrosion sensors are used are subject to meeting certain standards and/or requirements. For example, the National Electric Code (NEC), the National Electrical Manufacturers Association (NEMA), the International Electrotechnical Commission (IEC), and the Institute of Electrical and Electronics Engineers (IEEE) set standards as to electrical enclosures, wiring, and electrical connections. Use of example embodiments described herein meet (and/or allow a corresponding device and/or electrical enclosure to meet) such standards when required. In some (e.g., PV solar) applications, additional standards particular to that application may be met by the electrical enclosures in which example eddy current corrosion sensors are used.

In certain example embodiments, eddy current corrosion sensors can be used in spaces that are at least partially open (not fully enclosed). As discussed above, example embodiments can be used in hazardous environments or locations. Examples of a hazardous location in which example embodiments can be used can include, but are not limited to, an airplane hangar, a drilling rig (as for oil, gas, or water), a production rig (as for oil or gas), a refinery, a chemical plant, a power plant, a mining operation, and a steel mill. A hazardous environment can include an explosion-proof environment, which would require an electrical enclosure with an example eddy current corrosion sensor to meet one or more requirements, including but not limited to flame paths. Regardless of where and/or in what environments example embodiments are used, one or more components (e.g., inductor) of example eddy current corrosion sensors can be protected (e.g., hermetically sealed) since no electrical connections are required.

Further, if a component of a figure is described but not expressly shown or labeled in that figure, the label used for a corresponding component in another figure can be inferred to that component. Conversely, if a component in a figure is labeled but not described, the description for such component can be substantially the same as the description for the corresponding component in another figure. The numbering scheme for the various components in the figures herein is such that each component is a three or four digit number and corresponding components in other figures have the identical last two digits.

In addition, a statement that a particular embodiment (e.g., as shown in a figure herein) does not have a particular feature or component does not mean, unless expressly stated, that such embodiment is not capable of having such feature or component. For example, for purposes of present or future claims herein, a feature or component that is described as not being included in an example embodiment shown in one or more particular drawings is capable of being included in one or more claims that correspond to such one or more particular drawings herein.

Example embodiments of eddy current corrosion sensors will be described more fully hereinafter with reference to the accompanying drawings, in which example embodiments of eddy current corrosion sensors are shown. Eddy current corrosion sensors may, however, be embodied in many different forms and should not be construed as limited to the example embodiments set forth herein. Rather, these example embodiments are provided so that this disclosure will be thorough and complete, and will fully convey the scope of eddy current corrosion sensors to those of ordinary skill in the art. Like, but not necessarily the same, elements (also sometimes called components) in the various figures are denoted by like reference numerals for consistency.

Terms such as "first", "second", "top", "bottom", "side", "above", "below", "width", "length", "radius", "inner", and "outer" are used merely to distinguish one component (or part of a component or state of a component) from another. Such terms are not meant to denote a preference or a particular orientation, and are not meant to limit embodiments of eddy current corrosion sensors. In the following detailed description of the example embodiments, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

FIG. 1 shows a front view of an enclosure 100 (in this case, an explosion-proof electrical enclosure 100) in accordance with certain example embodiments. Referring now to FIG. 1, the enclosure 100 is in an open position (i.e., the enclosure cover 102 is not secured to the enclosure body 124). The enclosure 100 is located in an ambient environment 111 (e.g., a hazardous environment). The enclosure cover 102 can be secured to the enclosure body 124 by a number of fastening devices (not shown) located at a number of apertures 120 around the perimeter of the enclosure engagement surface 106 (also called a flange 106) of the enclosure cover 102 and around the perimeter of the enclosure engagement surface 108 (also called a flange 108) of the enclosure body 124.

When the enclosure cover 102 and the enclosure body 124 are in the closed position relative to each other, the enclosure engagement surface 108 of the enclosure body 124 abuts against the enclosure engagement surface 106 of the enclosure cover 102. When the enclosure 100 is an explosion-proof electrical enclosure, a flame path is formed between the enclosure engagement surface 108 of the enclosure body 124 and the enclosure engagement surface 106 of the enclosure cover 102. The enclosure body 124 forms a cavity 107 inside of which one or more devices 110 are disposed. When the enclosure cover 102 and the enclosure body 124 are in the closed position relative to each other, then the cavity 107 is substantially enclosed.

A fastening device may be one or more of a number of fastening devices, including but not limited to a bolt (which may be coupled with a nut), a screw (which may be coupled with a nut), and a clamp. In addition, one or more optional hinges 117 can be secured to one side of the enclosure cover 102 and a corresponding side of the enclosure body 124 so that, when all of the fastening devices are removed, as shown in FIG. 1, the enclosure cover 102 may swing outward (i.e., an open position) from the enclosure body 124 using the one or more hinges 117. In one or more example embodiments, there are no hinges, and the enclosure cover 102 can be completely separated from the enclosure body 124 when all of the fastening devices are removed.

The enclosure cover 102 and the enclosure body 124 may be made of any suitable material, including metal (e.g., alloy, stainless steel), plastic, some other material, or any combination thereof. The enclosure cover 102 and the enclosure body 124 may be made of the same material or different materials. In one or more example embodiments, on the end of the enclosure body 124 opposite the enclosure cover 102, one or more mounting brackets are affixed to the exterior of the enclosure body 124 to facilitate mounting the enclosure 100. Using the mounting brackets, the enclosure 100 may be mounted to one or more of a number of surfaces and/or elements, including but not limited to a wall, a control cabinet, a cement block, an I-beam, and a U-bracket.

There can be one or more conduits 105 that are coupled to a wall of the enclosure body 124 of the enclosure 100. Each conduit 105 can have one or more electrical conductors 109 (e.g., electrical cables) disposed therein, where one end of the electrical conductors 109 (also called electrical cables) are electrically coupled to one or more devices 110 (e.g., electrical device, mechanical device) disposed within the enclosure 100. As the electrical conductors 109 are subject to corrosion, the electrical conductors 109 can also be considered devices herein. There is a hole 116 that traverses the wall of the enclosure body 124 through which the electrical conductors 109 extend to make terminations within the cavity 107 of the enclosure 100.

In one or more example embodiments, the enclosure 100 of FIG. 1 includes a mounting plate 104 that is affixed to the back enclosure body 124 inside the enclosure 100. The mounting plate 104 may be configured to receive one or more devices 110 (e.g., electrical devices, mechanical devices) such that the one or more devices 110 are affixed to the mounting plate 104. The mounting plate 104 may include one or more apertures configured to receive coupling features (e.g., bolts) that may be used to affix a device 110 to the mounting plate 104. The mounting plate 104 may be made of any suitable material, including but not limited to the material of the enclosure body 124. In one or more example embodiments, some or all of the one or more devices 110 may be mounted directly to an inside wall of the enclosure 100 rather than to the mounting plate 104.

In this case, an enclosure 100 includes multiple example corrosion tracking systems 130. Specifically, the enclosure 100 of FIG. 1 includes corrosion tracking system 130-1, corrosion tracking system 130-2, and corrosion tracking system 130-3. Examples of what a corrosion tracking system 130 includes are described below with respect to the corrosion tracking system 230 of FIG. 2, the corrosion tracking system 330 of FIGS. 3A and 3B, and the corrosion tracking system 430 of FIGS. 4A and 4B. In this case, the enclosure 100 is located in an ambient environment 111 that has certain conditions (e.g., high humidity, low ventilation, high thermal mass) in which, over time, corrosion 103 can result in the cavity 107 of the enclosure 100. For example, as shown in FIG. 1, corrosion 103 has formed on the inner wall of the enclosure cover 102, the inner walls of the enclosure body 124, on the enclosure engagement surface 108, on the enclosure engagement surface 106, and on a number of components 110 disposed within the cavity 107 of the enclosure 100.

Corrosion 103 can cause one or more of a number of adverse conditions to devices 110 within the cavity 107 of the enclosure 100, as well as to the enclosure 100 itself. For example, the corrosion 103 can cause one or more devices 110 (or components thereof) disposed in the cavity 107 to seize, As another example, the corrosion 103 of wiring terminal connections (a type of device 110) can cause overheating at those terminal connections, which can degrade/destroy an associated device 110, cause a fire, and/or create some other adverse condition within the cavity 107. As yet another example, when the corrosion 103 collects on the enclosure engagement surface 108, and when the enclosure 100 is an explosion-proof enclosure, the flame path formed between the enclosure engagement surface 108 and the enclosure engagement surface 106 can be compromised, leading to a loss in explosion-proof integrity and creation of a safety hazard.

Many enclosures, regardless of the inclusion of a moisture monitoring, control, and/or notification system, are opened on a very infrequent basis. As a result, a user often does not realize that corrosion exists inside an enclosure and, if so, how severe the corrosion is. Often, systems known in the art for monitoring and/or controlling corrosion in an enclosure fail, usually because such systems are not designed to withstand the conditions (e.g., moisture) causing the corrosion over extended periods of time. Example embodiments are designed to be a safe and reliable system for notifying a user when corrosion within an enclosure is developing and how severe the corrosion is.

Figure 2:
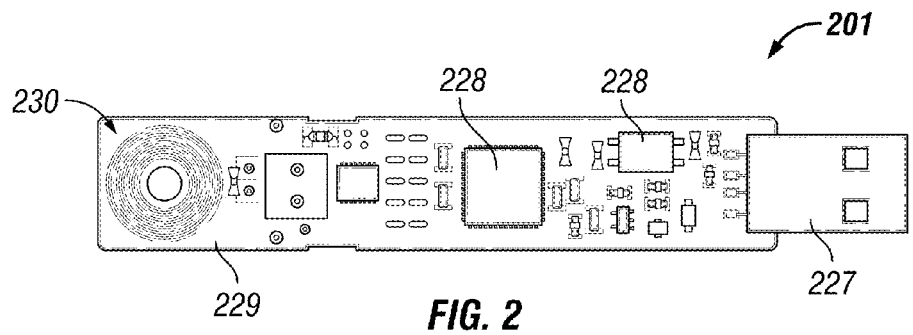
FIG. 2 shows a circuit module that includes at least a portion of a corrosion tracking system in accordance with certain example embodiments.

FIG. 2 shows a circuit module 201 that includes at least a portion of a corrosion tracking system in accordance with certain example embodiments. Referring to FIGS. 1 and 2, the circuit module 201 of FIG. 2 includes a connector 227 disposed at one end that connects to some other component (e.g., a power source, another circuit module) within the cavity 107 of an enclosure 100. Disposed on the circuit board 229 of the circuit module 201 are a number of integrated circuits 228 and at least part of a corrosion tracking system 230.

Figure 3A:
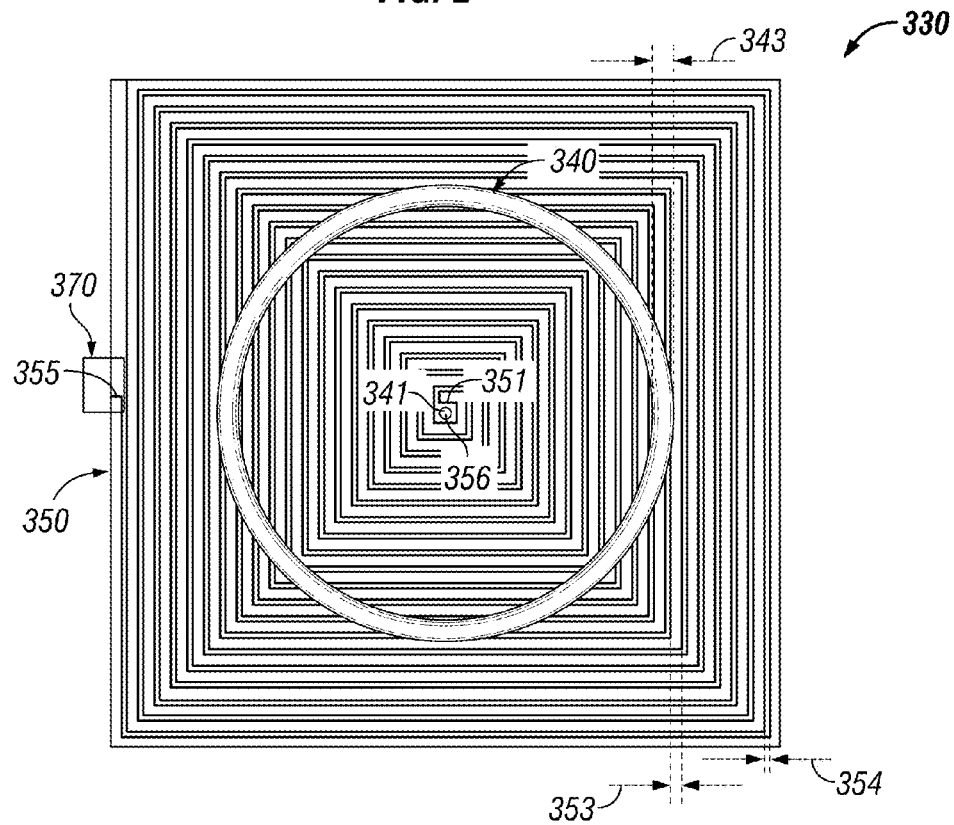
FIGS. 3A and 3B show a top view and a side view, respectively, of a corrosion tracking system in accordance with certain example embodiments.
Figure 3B:
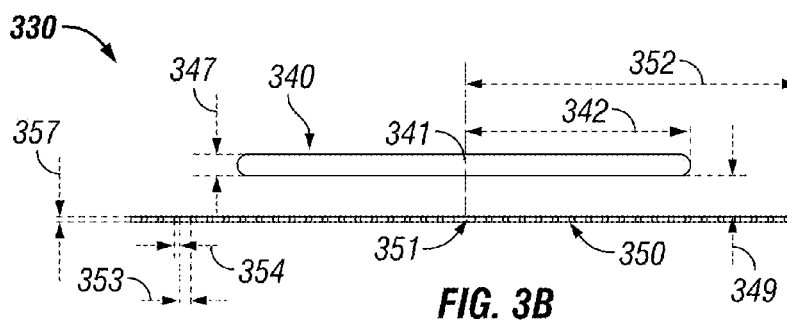

FIGS. 3A and 3B show a top view and a side view, respectively, of a corrosion tracking system 330 in accordance with certain example embodiments. Referring to FIGS. 1-3B, the corrosion tracking system 330 of FIGS. 3A and 3B can include a target component 340, an electrical circuit 350, and a sensor 370. In certain example embodiments, the target component 340 (also sometimes called a loop coupon 340) is a sacrificial component that is made of one or more materials that are subject to corrosion. The target component 340 forms a closed shape when viewed from above, as shown in FIG. 3A. Examples of a closed shape formed by the target component 340 can include, but is not limited to, a circle (as shown), an oval, a square, a hexagon, a triangle, a rectangle, and a random shape.

The target component 340 can have a height 347 and a width 343. The height 347 and/or the width 343 can be substantially uniform throughout. Alternatively, the height 347 and/or the width 343 can vary along the length of the target component 340. In addition, in some cases, the height 347 can be substantially the same as the width 343. The height 347 and/or the width 343 can be called any of a number of other names. For example, if the cross-sectional shape of the target component 340, when viewed axially along its length, is substantially circular, the height 347 and/or the width 343 can be called a diameter or a radius.

In any case, all of the particular characteristics (e.g., the composition, the shape, the height 347, the width 343, the radius 342, the perimeter, the approximate center 341 (when viewed from above)) of the target component 340, without corrosion, are known. The target component 340 is not coated, sealed, covered in an electrically-insulated jacket, or otherwise treated and/or manufactured so that corrosion of the materials that make up the target component 340 is not delayed or prohibited. In other words, example embodiments require the natural corrosion of the target component 340.

In some cases, there can be more than one target component 340 for a corrosion tracking system 330. In such a case, one target component 340 can be made of the same material or different material relative to one or more of the remaining target components 340. When there are multiple target components 340, there can be a single electrical circuit 350 that induces eddy currents in each target component 340. Alternatively, there can be multiple electrical circuits 350, where each electrical circuit 350 can induce eddy currents in one or more of the multiple target components 340.

In certain example embodiments, the electrical circuit 350 (also sometimes called an inductor 350) is a component that generates a magnetic field. The magnetic field generated by the electrical circuit 350 can induce eddy currents to flow within the target component 340 when the electrical circuit 350 and the target component 340 are placed some nominal distance 349 from each other, with the target component 340 being placed next to (e.g., above or below) the electrical circuit 350. The electrical circuit 350 can have a spiral-wound shape when viewed from above, as shown in FIG. 3A. Examples of a spiral-wound shape formed by the electrical circuit 350 can include, but are not limited to, a circle, an oval, a square (as shown), a hexagon, a triangle, a rectangle, and a random shape. The shape formed by the electrical circuit 350 can be the same as, or different than, the shape formed by the target component 340. Similarly, the cross-sectional shape of the electrical circuit 350 can be of any shape (e.g., circular, oval, square), be of any size, and/or have one or more of any of a number of features (e.g., protrusions, recesses).

The electrical circuit 350 can be a discrete component or can be integrated with another component of a system. For example, the electrical circuit 350 can be a discrete inductor. As another example, the electrical circuit 350 can be a trace on a printed circuit board. The electrical circuit 350 can have a first end 355 and a second end 356 that are not directly coupled to each other. In its spiral-wound shape, the electrical circuit 350 can be separated from itself by a distance 354, which can be substantially the same and/or variable along its length. A power source (not shown) can be electrically coupled to the first end 355 and/or the second end 356 to allow the magnetic field to be emitted by the electrical circuit 350.

The electrical circuit 350 can have a height 357 and a width 353. The height 357 and/or the width 353 can be substantially uniform throughout. Alternatively, the height 357 and/or the width 353 can vary along the length of the electrical circuit 350. In any case, all of the particular characteristics (e.g., the composition, the shape, the height 357, the width 353, the radius 352, the perimeter, the approximate center 351 (when viewed from above)) of the electrical circuit 350 are known. The electrical circuit 350 is coated, sealed, or otherwise treated so that corrosion of the materials that make up the electrical circuit 350 does not occur or occurs minimally over time. In other words, example embodiments require that the electrical circuit 350 delivers the magnetic field on a substantially consistent basis over time. In some cases, there can be more than one electrical circuit 350 for a corrosion tracking system 330.

In certain example embodiments, the electrical circuit 350 and the target component 340 have any of a number of orientations relative to each other. For example, the electrical circuit 350 and the target component 340 can be substantially parallel to each other, as shown in FIG. 3B. As another example, the approximate center 351 of the electrical circuit 350 and the approximate center 341 of the target component 340 can be substantially the same when viewed from above, as shown in FIG. 3A. As another example, as stated above, the electrical circuit 350 and the target component 340 can be separated from each other by a distance 349 (as shown in FIG. 3B) that allows eddy currents to flow in the target component 340 induced by the magnetic field generated by the electrical circuit 350. The radius 352 of the electrical circuit 350 can be greater than (as shown in FIGS. 3A and 3B), substantially equal to, or less than the radius 342 of the target component 340.

In certain example embodiments, the sensor 370 of the corrosion tracking system 330 measures the eddy currents flowing through the target component 340. As the target component 340 corrodes, the amount of eddy current flowing therethrough decreases. When the corrosion in the target component 340 becomes severe enough as to penetrate the entire height 347 and/or thickness 343 of some or all of the target component 340, an open circuit is created. In such a case, no eddy current flows within the target component 340. The sensor 370 can be part of the electrical circuit 350. Alternatively, the sensor 370 can be a separate component relative to the electrical circuit 350. The sensor 370 can be any type of sensing device using any type of technology to measure the eddy currents flowing in a target component 340. For example, the sensor 370 can be an inductance sensor that includes an inductance-to-digital converter.

The theory of eddy current sensor systems, such as the corrosion tracking system 330, is based on the use of magnetic fields. A current (usually, an alternating current) flows through an electrical circuit (e.g., electrical circuit 350), and this current generates a magnetic field (usually an alternating magnetic field) that emanates from the electrical circuit. With a target component (e.g., target component 340) placed proximate to the electrical circuit, the magnetic field that emanates from the electrical circuit induces small currents (also called eddy currents) in the target component. The eddy currents flowing through the target component generate a magnetic field that opposes the magnetic field generated by the electrical circuit. When alternating current is used, any of a number of frequencies (e.g., 12.5 kHz) can be used to induce eddy currents of known characteristics (e.g., level, frequency).

Figure 8:
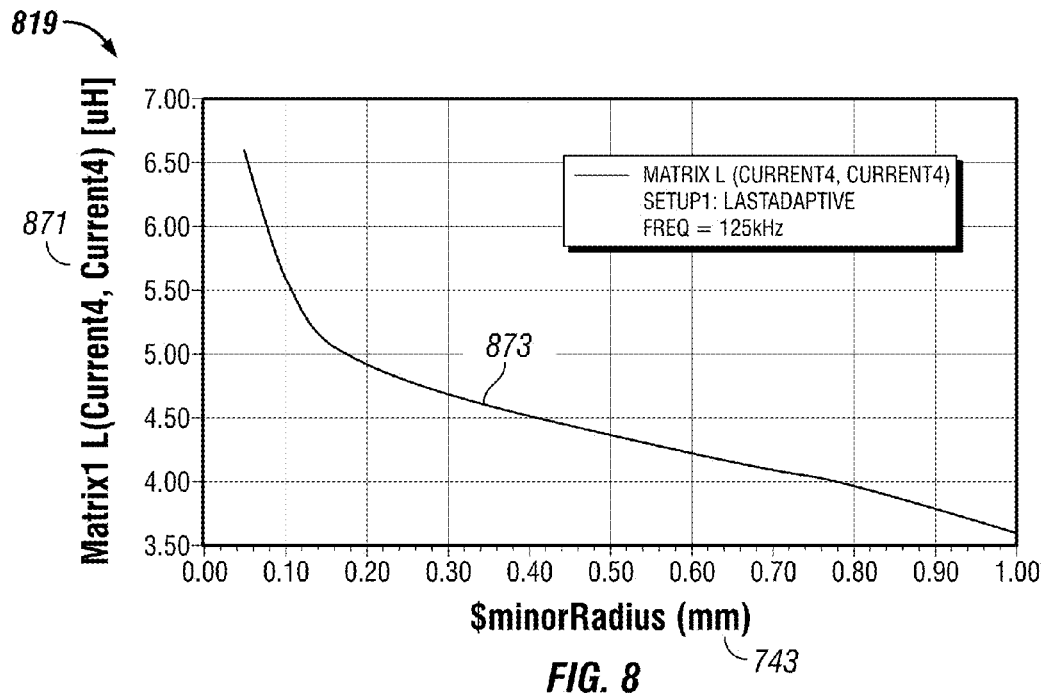
FIG. 8 shows a graph of the relationship between the cross-sectional radius of the target component and an amount of inductance in accordance with certain example embodiments.

In the current art, such a system is used to determine if there has been movement between the electrical circuit and the target component over time. In example embodiments, movement between the electrical circuit and the target component over time is not considered. Instead, measurements are taken over time of the eddy currents that flow through the target component 340. As shown in FIG. 8 below, as the target component 340 corrodes over time, the effective width 343 (i.e., the width 343 of the non-corroded portion of the target component 340) decreases. As a result, the amount of eddy current flowing through the target component 340 decreases over time.

Eventually, corrosion in the target component 340 can become so severe as to not allow any eddy current to flow through the target component 340, making the target component an open circuit. Therefore, by using example corrosion tracking systems 330, a user can determine that corrosion exists and/or is getting worse based on the amount of eddy current flowing through the target component 340, as measured by the sensor 370. Knowledge of factors such as the distance 349 between the target component 340 and the electrical circuit 350, the initial width 343 of the target component 340, the radius 342 of the target component 340, and the material of the target component 340 can help a user better determine the existence and/or the severity of corrosion occurring in the area proximate to the corrosion tracking system 330.

Figure 4A:
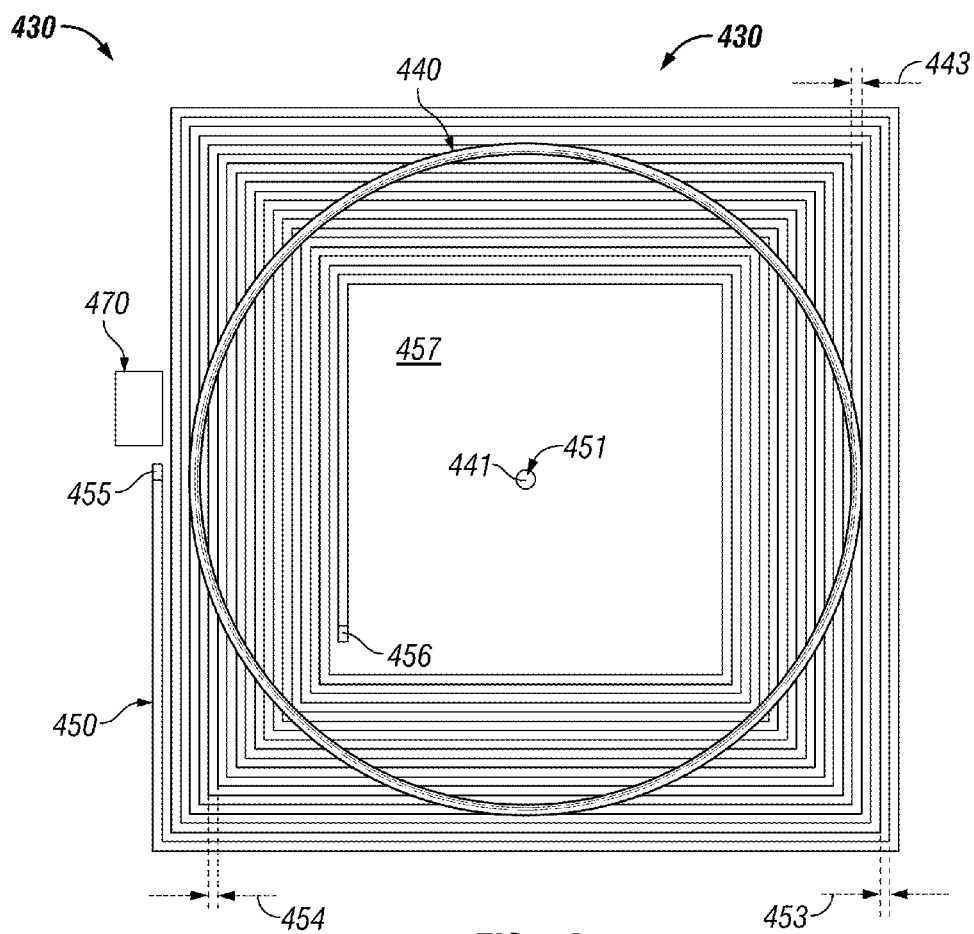
FIGS. 4A and 4B show a top view and a side view, respectively, of another corrosion tracking system in accordance with certain example embodiments.
Figure 4B:
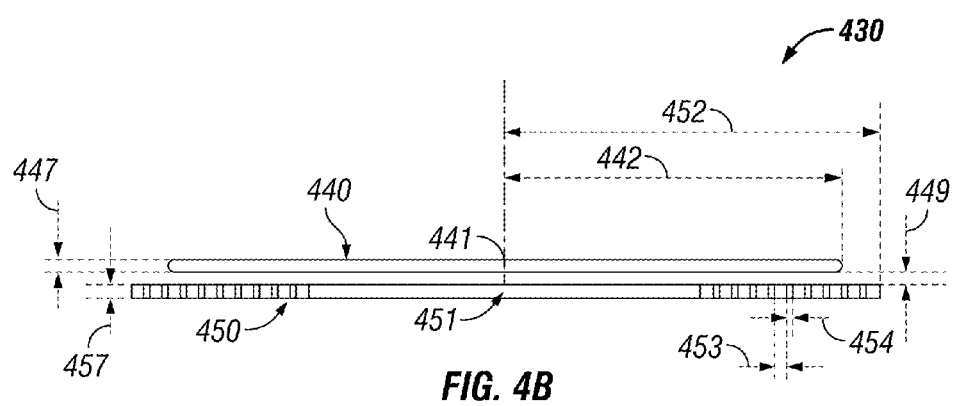

FIGS. 4A and 4B shows a top view and a side view, respectively, of another corrosion tracking system 430 in accordance with certain example embodiments. The corrosion tracking system 430 and its components are substantially the same as the corrosion tracking system 330 of FIGS. 3A and 3B, except as described below. For example, the radius 452 of the electrical circuit 450 of FIGS. 4A and 4B can be larger than the radius 352 of the electrical circuit 350 of FIGS. 3A and 3B. For example, the target component 440 can have a height 447 and a width 443, and can be formed around an approximate center 441. In addition, while the electrical circuit 450 of FIGS. 4A and 4B is a spiral-shaped square having a first end 455 coupled to a sensor 470, a width 453, and is separated from itself by a distance 454, as is the electrical circuit 350 of FIGS. 3A and 3B, the second end 456 of the electrical circuit 450 is not located at the approximate center 451 of the electrical circuit 450. As a result, there is an open space 457 within the spiral-shaped square formed by the electrical circuit 450. The electrical circuit 450 and the target component 440 are placed some nominal distance 449 from each other, with the target component 440 being placed next to (e.g., above or below) the electrical circuit 450.

Further, the radius 442 of the target component 440 is larger than the radius 342 of the target component 340. Also, the difference between the radius 452 of the electrical circuit 450 and the radius 442 of the target component 440 is less than the difference between the radius 352 of the electrical circuit 350 and the radius 342 of the target component 340. Regardless of the configuration of each of the components of example corrosion tracking systems, and regardless of the orientation of the components of example corrosion tracking systems relative to each other, example embodiments can be used to detect and track corrosion that occurs over time in a volume of space proximate to the corrosion tracking system.

Figure 5:
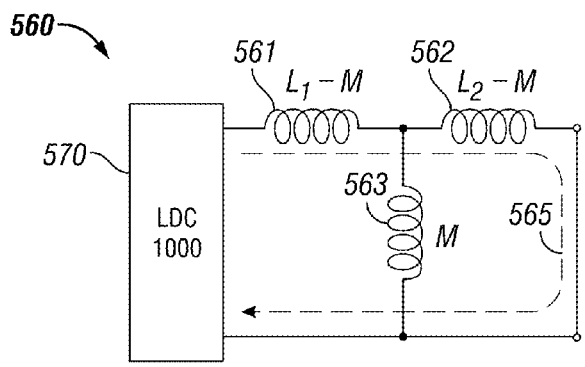
FIG. 5 shows a schematic of a corrosion tracking system during moderately corrosive operating conditions in accordance with certain example embodiments.
Figure 6:
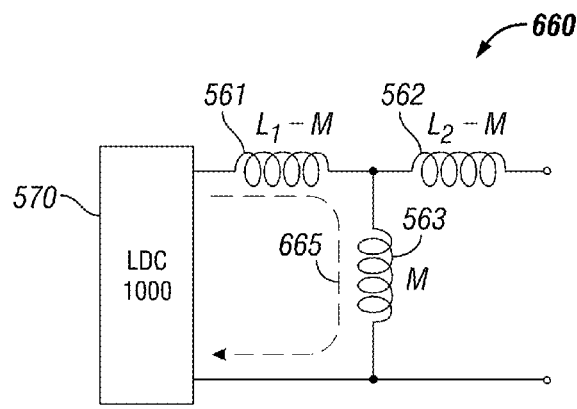
FIG. 6 shows a schematic of a corrosion tracking system during severely corrosive operating conditions in accordance with certain example embodiments.

FIGS. 5 and 6 show schematics of how measurements by a sensor 570 can detect and track corrosion. Specifically, FIG. 5 shows a schematic 560 of a corrosion tracking system during moderately corrosive operating conditions in accordance with certain example embodiments. FIG. 6 shows a schematic 660 of a corrosion tracking system during severely corrosive operating conditions in accordance with certain example embodiments. Referring to FIGS. 1-6, the schematic 560 shows a sensor 570 that is connected in series with inductor 561 and in parallel with inductor 562 and inductor 563. Inductor 561 represents the difference between the inductance of the electrical circuit 350 and the mutual inductance between the electrical circuit 350 and the target component 340. Inductor 562 represents the difference between the inductance of the target component 340 and the mutual inductance between the electrical circuit 350 and the target component 340. Inductor 563 represents the mutual inductance between the electrical circuit 350 and the target component 340.

When the target component 340 is not significantly corroded, as shown in FIG. 5, inductor 562 is less than inductor 563. Specifically, the inductance of the target component 340 is significantly less than the mutual inductance between the electrical circuit 350 and the target component 340. As a result, the current 565 read by the sensor 570 flows through inductor 561 and inductor 562. Put another way, the current 565 bypasses inductor 563.

When the target component 340 is significantly corroded, the width 343 and/or the height 347 of the target component 340 is reduced. As a result, the inductance of the target component 340 increases, ultimately creating an open when the corrosion of the target component 340 is complete. Consequently, as shown in FIG. 6, the current 665 read by the sensor 570 flows through inductor 561 and inductor 563, and so bypasses inductor 562.

Figure 7:
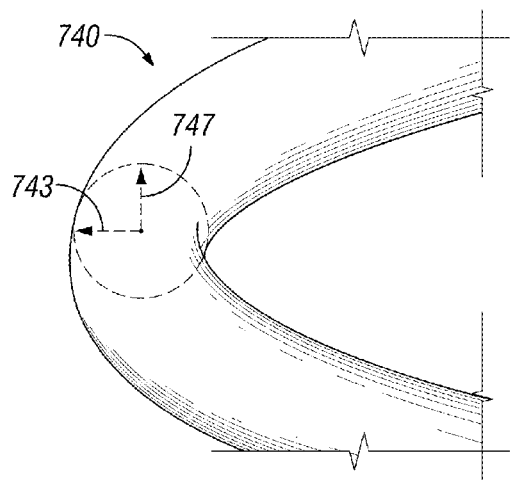
FIG. 7 shows a detailed view of a target component in accordance with certain example embodiments.

FIG. 7 shows a detailed view of a target component 740 in accordance with certain example embodiments. Referring to FIGS. 1-7, the target component 740 is substantially the same as the target components described above. In this case, the target component 740 of FIG. 7 has a cross-sectional shape, when viewed axially along its length, that is substantially circular. As such, the height 747 and the width 743 are shown as a radius. The height 747 and the width 743 can be substantially the same as each other.

FIG. 8 shows a graph 819 of the relationship between the cross-sectional radius 743 of the target component 740 of FIG. 7 and an amount of inductance 871 in the target component 740 in accordance with certain example embodiments. All of the readings recorded in the curve 873 of the graph 819 are at a frequency of approximately 125 kHz. The curve 873 of the graph 819 shows that the inductance 871 in the target component 740 is lowest (in this case, approximately 3.6 uH) when the radius 743 of the target component 740 is greatest (in this case, approximately 1.00 mm).

As corrosion sets in and reduces the radius 743 of the target component 740, the inductance 871 in the target component 740 increases in a substantially linear relationship until where the radius 743 of the target component 740 is approximately 0.15 mm, which corresponds to an inductance 871 in the target component 740 of approximately 5.1 uH. As the radius 743 of the target component 740 continues to decrease because of increased corrosion, there is a substantially linear relationship between the radius 743 of the target component 740 and the inductance 871 in the target component 740, but with a more severe negative slope. Specifically, as shown in the graph 819, as the radius 743 of the target component 740 decreases to approximately 0.05 mm, the inductance 871 in the target component 740 increases to approximately 6.6 uH.

Figure 9:
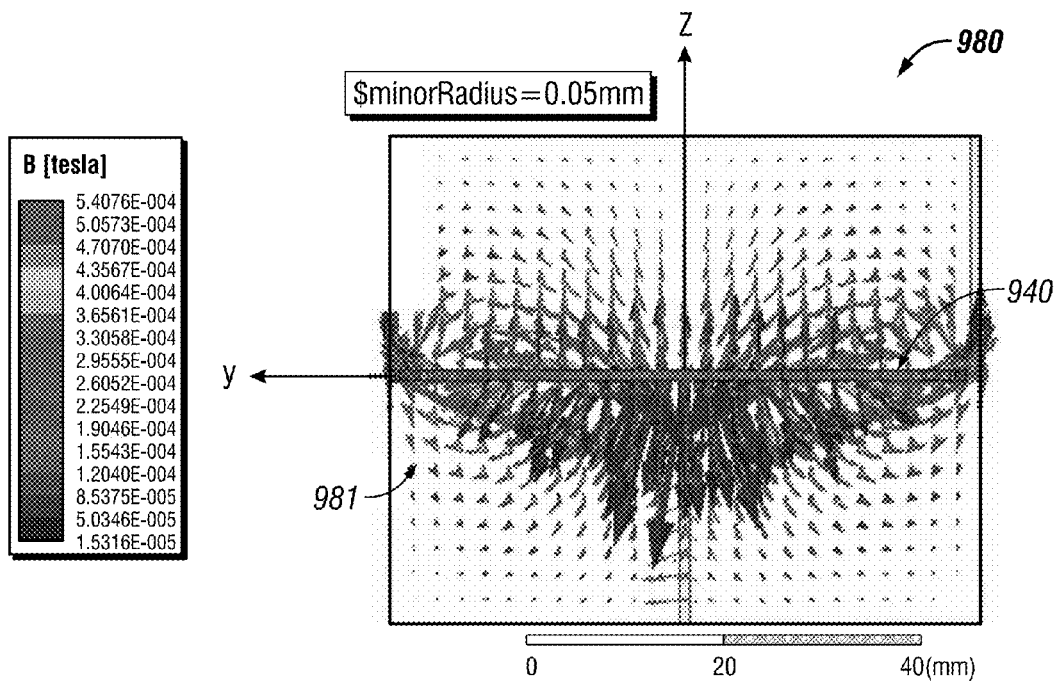
FIGS. 9 and 10 each show a graph of a magnetic field generated by eddy current induced in a target component in accordance with certain example embodiments.
Figure 10:
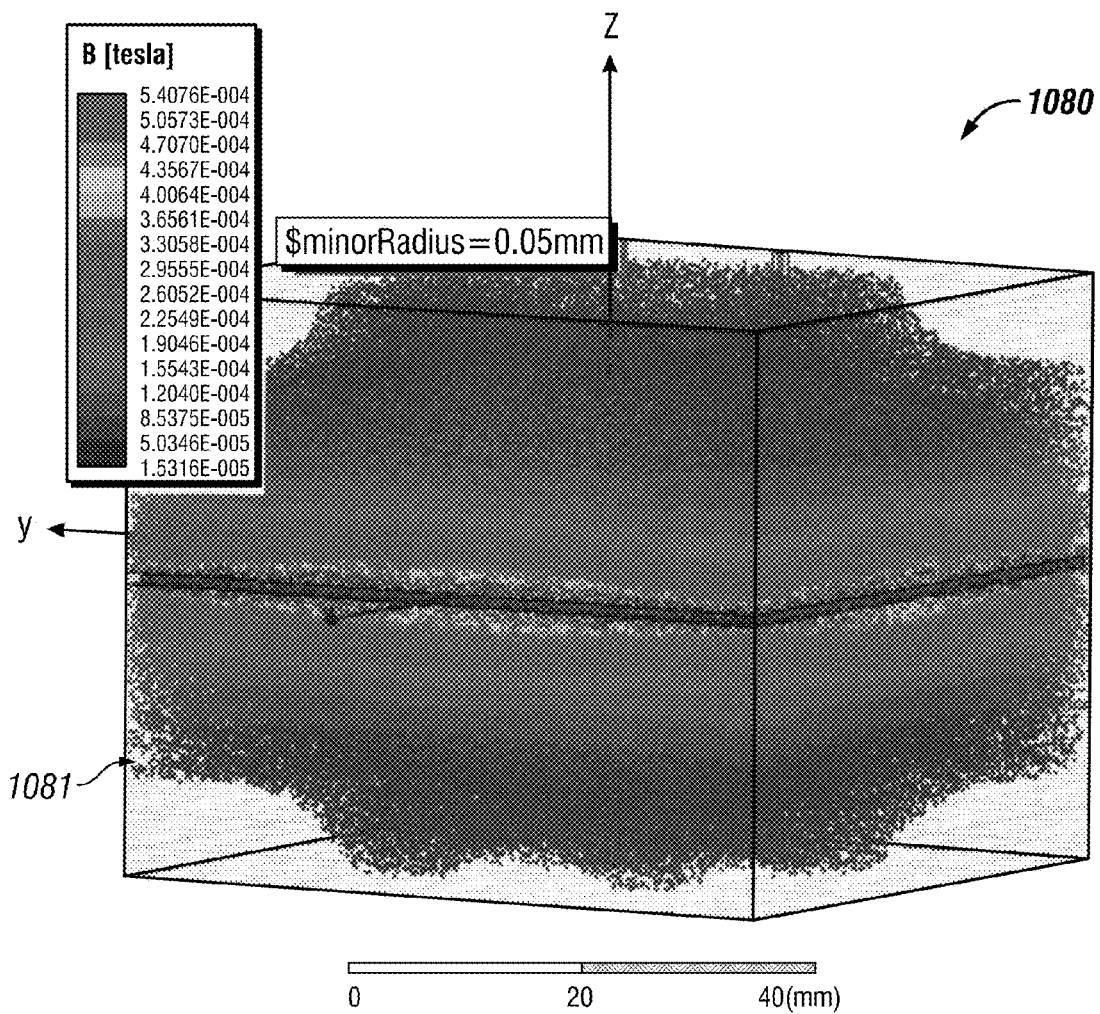

FIGS. 9 and 10 each show a graph of a magnetic field generated by eddy current induced in a target component in accordance with certain example embodiments. Referring to FIGS. 1-10, the graph 980 of FIG. 9 shows the strength and direction of the magnetic field 981 emitted by a target component 940 when the radius of the target component 940 is approximately 0.05 mm. The graph 1080 of FIG. 10 shows the strength of the magnetic field 1081 emitted by a target component when the radius of the target component is approximately 0.05 mm.

Figure 11:
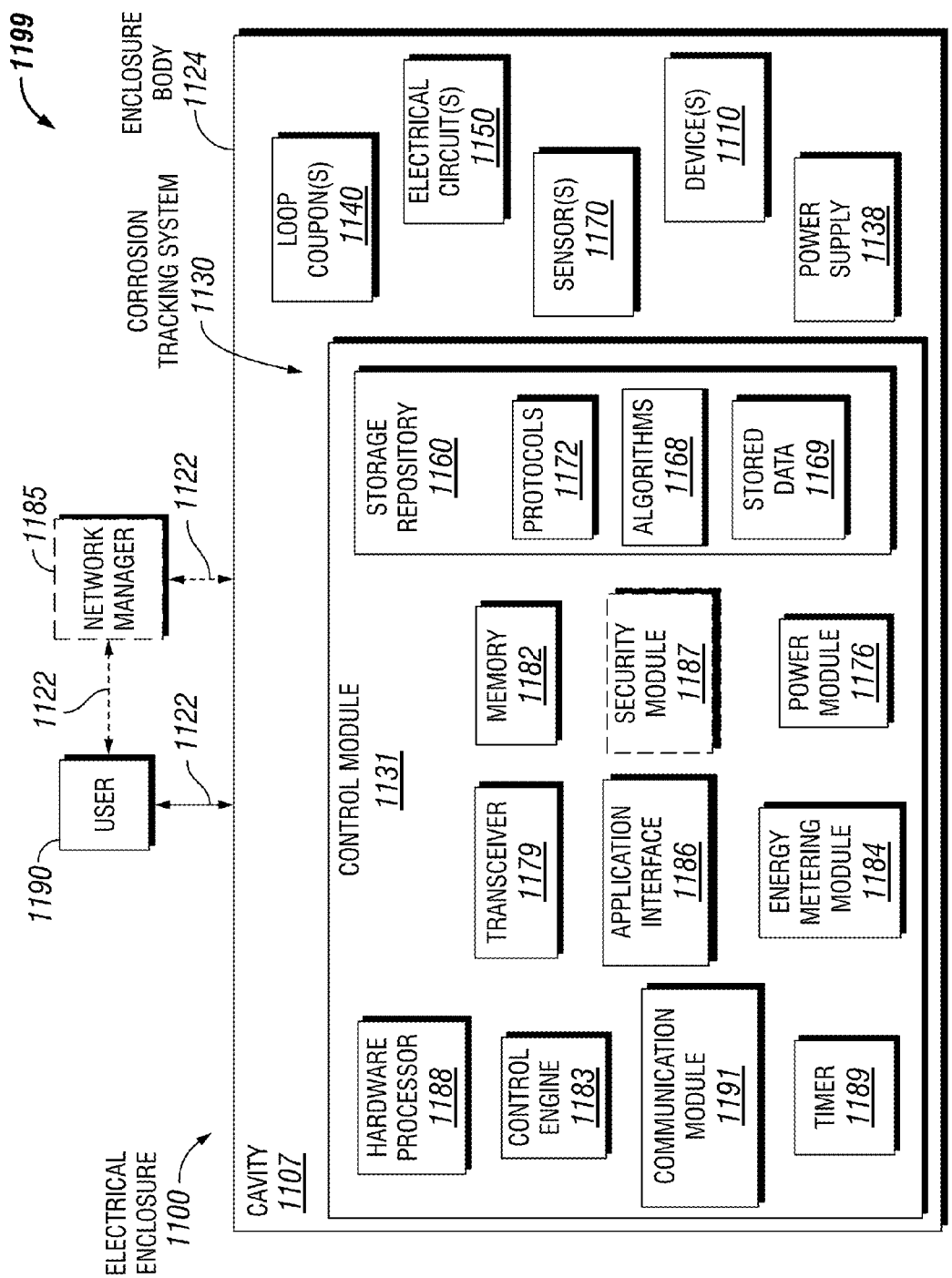
FIG. 11 shows a system diagram that includes a controller in accordance with certain example embodiments.

FIG. 11 shows a diagram of a system 1199 that includes a controller in accordance with certain example embodiments. Referring to FIGS. 1-11, in addition to the electrical enclosure 1100, the system 1199 of FIG. 11 can include a user 1190 and an optional network manager 1185. The electrical enclosure 1100 can include one or more devices 1110, a power supply 1138, and a corrosion tracking system 1130. The corrosion tracking system 1130 can include, for example, a control module 1131, one or more loop coupons 1140, one or more electrical circuits 1150, and one or more sensors 1170. The control module 1131 can include one or more of a number of components. Such components, can include, but are not limited to, a control engine 1183, a communication module 1191, a timer 1189, a power module 1176, an energy metering module 1184 (also called, more simply, a metering module 1184 herein), a storage repository 1160, a hardware processor 1188, a memory 1182, a transceiver 1179, an application interface 1186, and, optionally, a security module 1187. The components shown in FIG. 11 are not exhaustive, and in some embodiments, one or more of the components shown in FIG. 11 may not be included in an example electrical enclosure 1100. Any component of the example electrical enclosure 1100 can be discrete or combined with one or more other components of the electrical enclosure 1100.

The user 1190 is the same as a user defined above. The user 1190 interacts with (e.g., sends instructions to, sends settings to, receives data from) the electrical enclosure 1100 (including any portions thereof, such as the control module 1131, the sensors 1170) via the application interface 1186 and one or more communication links 1122 (described below). The user 1190 can also interact with a network manager 1185. Interaction between the user 1190 and the electrical enclosure 1100 and/or the network manager 1185 can be conducted using communication links 1122. The communication links 1122 can transmit signals (e.g., electrical power, communication signals, control signals, data) between the electrical enclosure 1100, the user 1190, and the network manager 1185.

The network manager 1185 is a device or component that can communicate with the control module 1131. For example, the network manager 1185 can send instructions to the control module 1131 of the electrical enclosure 1100 as to when current should be sent through the loop coupon 1140. As another example, the network manager 1185 can receive data associated with the operation of the corrosion tracking system 1130 of the electrical enclosure 1100. Such data can be used for any of a number of purposes, such as determining when maintenance should be performed on a device 1110, the corrosion tracking system 1130 (or portions thereof), or some other component within the cavity 1107 formed by the enclosure body 1124 of the electrical enclosure 1100.

The electrical enclosure 1100 can use one or more of a number of communication protocols (a type of protocol 1172). The electrical enclosure 1100 can include and/or be coupled to one or more sensors 1170. A sensor 1170 can be substantially similar to a sensor described above. These sensors 1170 can measure one or more parameters in and/or around the electrical enclosure 1100. Examples of such parameters can include, but are not limited to, current, temperature, and relative humidity. For example, a sensor 1170 can measure an amount of eddy current flowing through an electrical circuit 1150. In some cases, a sensor 1170 can send a parameter (for example, to the control module 1131) in addition to measuring a parameter.

The devices 1110, the electrical circuits 1150, and the loop coupons 1140 of FIG. 11 can be substantially the same as the devices, the electrical circuits, and the loop coupons described above. The power supply 1138 of the electrical enclosure 1100 can send power, control, and/or communication signals to the control module 1131, the sensors 1170, the devices 1110, and/or the loop coupons 1140. The power supply 1138 can include one or more components. Examples of components of a power supply 1138 can include, but are not limited to, a transformer, a generator, a battery, an electrical receptacle, an electrical cable, an electrical conductor, a fuse, a breaker, and an inductor. The power supply 1138 can be a source of independent power generation. For example, the power supply 1138 can include an energy storage device (e.g., a battery, a supercapacitor). As another example, the power supply 1138 can include photovoltaic solar panels. In addition, or in the alternative, the power supply 1138 can receive power from an independent power supply. The independent power supply can be any source of power that is independent of the power supply 1138. Examples of a power supply can include, but are not limited to, an energy storage device, a step-down transformer, a feed to a building, a feed from a circuit panel, and an independent generation source (e.g., photovoltaic panels, a heat exchanger).

In certain example embodiments, the power supply 1138 sends power, control, and/or communication signals to, and receives power, control, and/or communication signals from, the control module 1131 of the electrical enclosure 1100. In this way, the control module 1131 of the electrical enclosure 1100 can control the amount of power sent by the power supply 1138 to the sensors 1170, the devices 1110, and/or the loop coupon 1140.

The control module 1131 of the electrical enclosure 1100 can interact (e.g., periodically, continually, randomly) with the user 1190, the network manager 1185 and/or one or more other components of the corrosion tracking system 1130. The user 1190, the network manager 1185, and/or the other components of the corrosion tracking system 1130 can interact with the control module 1131 of the electrical enclosure 1100 using the application interface 1186 and/or the communication links 1122 in accordance with one or more example embodiments. For example, the application interface 1186 of the control module 1131 can receive data (e.g., information, communications, instructions) from and sends data (e.g., information, communications, instructions) to the user 1190 and the network manager 1185.

The control module 1131, the user 1190, and/or the network manager 1185 can use their own system or share a system in certain example embodiments. Such a system can be, or contain a form of, an Internet-based or an intranet-based computer system that is capable of communicating with various software. A computer system includes any type of computing device and/or communication device, including but not limited to the control module 1131. Examples of such a system can include, but are not limited to, a desktop computer with LAN, WAN, Internet or intranet access, a laptop computer with LAN, WAN, Internet or intranet access, a smart phone, a server, a server farm, an android device (or equivalent), a tablet, smartphones, and a personal digital assistant (PDA). Such a system can correspond to a computer system as described below with regard to FIG. 12.

Further, as discussed above, such a system can have corresponding software (e.g., user software, network manager software, control module software). The software can execute on the same or a separate device (e.g., a server, mainframe, desktop personal computer (PC), laptop, PDA, television, cable box, satellite box, kiosk, telephone, mobile phone, or other computing devices) and can be coupled by the communication network (e.g., Internet, Intranet, Extranet, Local Area Network (LAN), Wide Area Network (WAN), or other network communication methods) and/or communication channels, with wire and/or wireless segments according to some example embodiments. The software of one system can be a part of, or operate separately but in conjunction with, the software of another system within the system 1199.

As discussed above, the electrical enclosure 1100 can include an enclosure body 1124 and an enclosure cover. The enclosure body 1124 can include at least one wall that forms a cavity 1107, and the cavity 1107 becomes enclosed when the enclosure cover couples to the enclosure body 1124. The enclosure body 1124 of the electrical enclosure 1100 can be used to house one or more components (e.g., power supply 1138, sensors 1170, loop coupon 1140, electrical circuit 1150) of the electrical enclosure 1100, including one or more components of the control module 1131. For example, as shown in FIG. 11, the control module 1131 (which in this case includes the control engine 1183, the communication module 1191, the storage repository 1160, the hardware processor 1188, the memory 1182, the transceiver 1179, the application interface 1186, the timer 1189, the energy metering module 1184, the power module 1176, and the optional security module 1187) can be disposed within the cavity 1107 formed by the enclosure body 1124. In alternative embodiments, any one or more of these or other components (or portions thereof) of the electrical enclosure 1100 can be disposed on the enclosure body 1124 and/or remotely from the enclosure body 1124.

The storage repository 1160 can be a persistent storage device (or set of devices) that stores software and data used to assist the control module 1131 in communicating with the user 1190, and the network manager 1185 within the system 1199. In one or more example embodiments, the storage repository 1160 stores one or more protocols 1172 (which can include communication protocols), algorithms 1168, and stored data 1169. The protocols 1172 are generally a process or procedure by which the control module 1131 (or portions thereof) operates under a given set of conditions (e.g., time, readings by a sensor 1170, measurements by the energy metering module 1184).

When the protocols 1172 are communication protocols, the communication protocols can be any of a number of protocols that are used to send and/or receive data between the control module 1131, the user 1190, and the network manager 1185. One or more of the protocols 1172 can be a time-synchronized protocol. Examples of such time-synchronized protocols can include, but are not limited to, a highway addressable remote transducer (HART) protocol, a wirelessHART protocol, and an International Society of Automation (ISA) 100 protocol. In this way, one or more of the protocols 1172 can provide a layer of security to the data transferred within the system 1199.

The algorithms 1168 can be any procedures (e.g., a series of method steps), formulas, logic steps, mathematical models, and/or other similar operational procedures that the control engine 1183 of the control module 1131 follows based on certain conditions at a point in time. For example, the control module 1131 can use an algorithm 1169 to measure (using the energy metering module 1184) one or more parameters (e.g., current) for power that flows through the electrical circuit 1150, compare this with the resulting amount of eddy current flowing through the loop coupon 1140 (as measured by a sensor 1170), and evaluate the amount of corrosion being experienced by a device 1110 located proximate to the electrical circuit 1150 within the cavity 1107.

As another example, the control module 1131 can use another algorithm 1168 to continuously monitor the measurements made by the sensors 1170, and use this data to determine the operating parameters of the corrosion tracking system 1130. As another example, the control module 1131 can use yet another algorithm 1168 to measure one or more parameters of the corrosion tracking system 1130, and use this data to determine whether one or more characteristics (e.g., moisture content) is within acceptable parameters (also called threshold values, and also part of the stored data 1169).

Stored data 1169 can be any data associated with the electrical enclosure 1100 (including any components thereof), any measurements taken by the sensors 1170, measurements taken by the energy metering module 1184, time measured by the timer 1189, stored data 1169 (e.g., threshold values, historical measured values), current ratings for the power supply 1138, nameplate information associated with the various components (e.g., devices 1110, loop coupon 1140, electrical circuit 1150, sensors 1170) within the electrical enclosure 1100, performance history of the one or more of the various components within the electrical enclosure 1100, results of previously run or calculated algorithms 1168, and/or any other suitable data. The stored data 1169 can be associated with some measurement of time derived, for example, from the timer 1189.

Examples of a storage repository 1160 can include, but are not limited to, a database (or a number of databases), a file system, a hard drive, flash memory, some other form of solid state data storage, or any suitable combination thereof. The storage repository 1160 can be located on multiple physical machines, each storing all or a portion of the protocols 1172, the algorithms 1168, and/or the stored data 1169 according to some example embodiments. Each storage unit or device can be physically located in the same or in a different geographic location.

The storage repository 1160 can be operatively connected to the control engine 1183. In one or more example embodiments, the control engine 1183 includes functionality to communicate with the user 1190 and the network manager 1185 in the system 1199. More specifically, the control engine 1183 sends information to and/or receives information from the storage repository 1160 in order to communicate with the user 1190 and the network manager 1185. As discussed below, the storage repository 1160 can also be operatively connected to the communication module 1191 in certain example embodiments.

In certain example embodiments, the control engine 1183 of the control module 1131 controls the operation of one or more components (e.g., the communication module 1191, the timer 1189, the transceiver 1179) of the control module 1131. For example, the control engine 1183 can put the communication module 1191 in "sleep" mode when there are no communications between the control module 1131 and another component (e.g., the user 1190) in the system 1199 or when communications between the control module 1131 and another component in the system 1199 follow a regular pattern. In such a case, power consumed by the control module 1131 is conserved by only enabling the communication module 1191 when the communication module 1191 is needed.

As another example, the control engine 1183 can acquire the current time using the timer 1189. The timer 1189 can enable the control module 1131 to control the power supply 1138 (and so also the corrosion tracking system 1130) of the electrical enclosure 1100, even when the control module 1131 has no communication with the user 1190 and/or the network manager 1185. In certain example embodiments, the timer 1189 can track the amount of time that the corrosion tracking system 1130 (including any one or more components thereof) is operating. In such a case, the control engine 1183 can control the power supply 1138 (and so also the corrosion tracking system 1130) based on an amount of time measured by the timer 1189.

In addition to the aspects and capabilities of the control module 1131 described above, the control engine 1183 of the control module 1131 can provide direct or indirect control of any aspect of operation of the corrosion tracking system 1130. For example, the control engine 1183 can control the operation of the devices 1110, a sensor 1170, the loop coupon 1140, the power supply 1138, and/or any other component within the cavity 1107 of the electrical enclosure 1100.

In certain example embodiments, the control engine 1183 of the control module 1131 controls the power supply 1138 to regulate the timing and amount of current that the power supply 1138 sends through one or more of the electrical circuits 1150. The control engine 1183 can also control one or more of the sensors 1170 to measure an amount of eddy current that flows through one or more of the loop coupons 1140. The control engine 1183 can also determine, using measurements made by the sensors 1170 and data stored in the storage repository 1160, an amount of corrosion that is occurring in a loop coupon 1140, and so infer an amount of corrosion that one or more of the devices 1110 can be experiencing.

In certain example embodiments, the control engine 1183 can analyze data stored in the storage repository 1160 using one or more algorithms 1168 stored in the storage repository 1160. In this way, the control engine 1183 can provide a historical analysis and/or a predictive analysis to a user 1190 and/or the network manager 1185 regarding the corrosion tracking system 1130 and/or the devices 1110 in the system 1199. In such a case, for example, the control engine 1183 can establish a preventative maintenance program for the electrical enclosure 1100, including any specific components (e.g., the power supply 1138, a component of the corrosion tracking system 1130, the devices 1110) thereof.

The control engine 1183 can provide control, communication, and/or other similar signals to the user 1190 and/or the network manager 1185. Similarly, the control engine 1183 can receive control, communication, and/or other similar signals from the user 1190 and/or the network manager 1185. The control engine 1183 can control the corrosion tracking system 1130 automatically (for example, based on one or more algorithms 1168 and/or protocols 1172 stored in the storage repository 1160) and/or based on control, communication, and/or other similar signals received from of another component (e.g., the network manager 1185) of the system 1199 through the communication links 1122. The control engine 1183 may include a printed circuit board, upon which the hardware processor 1188 and/or one or more discrete components of the control module 1131 can be positioned.

In certain example embodiments, the control engine 1183 can include an interface that enables the control engine 1183 to communicate with one or more components (e.g., communication module 1191) of the electrical enclosure 1100 and/or another component (e.g., the user 1190, the network manager 1185) of the system 1199. Such an interface can operate in conjunction with, or independently of, the protocols 1172 used to communicate between the control module 1131, the user 1190, and/or the network manager 1185.

The control engine 1183 can operate in real time. In other words, the control engine 1183 of the control module 1131 can process, send, and/or receive communications with the user 1190 and/or the network manager 1185 as any changes (e.g., discrete, continuous) occur within the system 1199. Further, the control engine 1183 of the control module 1131 can, at substantially the same time, control the corrosion tracking system 1130 (including, for example, a sensor 1170 and a loop coupon 1140), the power supply 1138, and the network manager 1185 based on such changes. In addition, the control engine 1183 of the control module 1131 can perform one or more of its functions continuously. For example, the control module 1131 can continuously use and update protocols 1172 and/or algorithms 1168. As another example, the control module 1131 can continuously control the power supply 1138 of the electrical enclosure 1100. In such a case, any updates or changes can be used by the control module 1131 in adjusting a component of the corrosion tracking system 1130 in real time.

The control engine 1183 (or other components of the control module 1131) can also include one or more hardware and/or software architecture components to perform its functions. Such components can include, but are not limited to, a universal asynchronous receiver/transmitter (UART), a universal synchronous receiver/transmitter (USRT), a serial peripheral interface (SPI), a direct-attached capacity (DAC) storage device, an analog-to-digital converter, an inter-integrated circuit ($I^2C$), and a pulse width modulator (PWM).

In certain example embodiments, the communication module 1191 of the control module 1131 determines and implements the communication protocol (e.g., from the protocols 1172 of the storage repository 1160) that is used when the control engine 1183 communicates with (e.g., sends signals to, receives signals from) the user 1190 and/or the network manager 1185. In some cases, the communication module 1191 accesses the protocols 1172 and/or the algorithms 1168 to determine which communication protocol is within the capability of the recipient of a communication sent by the control engine 1183. In addition, the communication module 1191 can interpret the communication protocol of a communication received by the control module 1131 so that the control engine 1183 can interpret the communication.

The communication module 1191 can send data directly to and/or retrieve data directly from the storage repository 1160. Alternatively, the control engine 1183 can facilitate the transfer of data between the communication module 1191 and the storage repository 1160. The communication module 1191 can also provide encryption to data that is sent by the control module 1131 and decryption to data that is received by the control module 1131. The communication module 1191 can also provide one or more of a number of other services with respect to data sent from and received by the control module 1131. Such services can include, but are not limited to, data packet routing information and procedures to follow in the event of data interruption.

The timer 1189 of the control module 1131 can track clock time, intervals of time, an amount of time, and/or any other measure of time. The timer 1189 can also count the number of occurrences of an event, whether with or without respect to time. Alternatively, the control engine 1183 can perform the counting function. The timer 1189 is able to track multiple time measurements concurrently. The timer 1189 can track time periods based on an instruction received from the control engine 1183, based on an instruction received from the user 1190, based on an instruction programmed in the software for the control module 1131, based on some other condition or from some other component, or from any combination thereof.

The timer 1189 can be configured to track time when there is no power delivered to the control module 1131 (e.g., the power module 1176 malfunctions) using, for example, a super capacitor or a battery backup. In such a case, when there is a resumption of power delivery to the control module 1131, the timer 1189 can communicate any aspect of time to the control module 1131. In such a case, the timer 1189 can include one or more of a number of components (e.g., a super capacitor, an integrated circuit) to perform these functions.

The energy metering module 1184 of the control module 1131 measures one or more components of energy (e.g., current, voltage, resistance, VARs, watts) associated with the electrical enclosure 1100 (including the power supply 1138 and the devices 1110) at one or more points in the system 1199. The energy metering module 1184 can include any of a number of measuring devices and related devices, including but not limited to a voltmeter, an ammeter, a power meter, an ohmmeter, a current transformer, a potential transformer, and electrical wiring. The energy metering module 1184 can measure a component of energy continuously, periodically, based on the occurrence of an event, based on a command received from the control engine 1183, based on measurements captured by the sensors 1170, and/or based on some other factor.

The power module 1176 of the control module 1131 provides power to one or more other components (e.g., timer 1189, control engine 1183) of the control module 1131. In certain example embodiments, the power module 1176 receives power from the power supply 1138. The power module 1176 can include one or more of a number of single or multiple discrete components (e.g., transistor, diode, resistor), and/or a microprocessor. The power module 1176 may include a printed circuit board, upon which the microprocessor and/or one or more discrete components are positioned. In some cases, the power module 1176 can include one or more components that allow the power module 1176 to measure one or more elements of power (e.g., voltage, current) that is delivered to and/or sent from the power module 1176.

The power module 1176 can include one or more components (e.g., a transformer, a diode bridge, an inverter, a converter) that receives power (for example, through an electrical cable) from a source (e.g., the power supply 1138) and generates power of a type (e.g., alternating current, direct current) and level (e.g., 12V, 24V, 120V) that can be used by the other components of the control module 1131. The power module 1176 can use a closed control loop to maintain a preconfigured voltage or current with a tight tolerance at the output. The power module 1176 can also protect the rest of the electronics (e.g., hardware processor 1188, transceiver 1179) from surges generated in the line. In addition, or in the alternative, the power module 1176 can be a source of power in itself to provide signals to the other components of the control module 1131. For example, the power module 1176 can be a battery. As another example, the power module 1176 can be a localized photovoltaic power system.

The hardware processor 1188 of the control module 1131 executes software in accordance with one or more example embodiments. Specifically, the hardware processor 1188 can execute software on the control engine 1183 or any other portion of the control module 1131, as well as software used by the user 1190 and/or the network manager 1185. The hardware processor 1188 can be an integrated circuit, a central processing unit, a multi-core processing chip, a multi-chip module including multiple multi-core processing chips, or other hardware processor in one or more example embodiments. The hardware processor 1188 is known by other names, including but not limited to a computer processor, a microprocessor, and a multi-core processor.

In one or more example embodiments, the hardware processor 1188 executes software instructions stored in memory 1182. The memory 1182 includes one or more cache memories, main memory, and/or any other suitable type of memory. The memory 1182 is discretely located within the control module 1131 relative to the hardware processor 1188 according to some example embodiments. In certain configurations, the memory 1182 can be integrated with the hardware processor 1188.

In certain example embodiments, the control module 1131 does not include a hardware processor 1188. In such a case, the control module 1131 can include, as an example, one or more field programmable gate arrays (FPGA) and/or one or more insulated-gate bipolar transistors (IGBTs). As another example, the control module 1131 can include one or more integrated circuits (ICs). Using FPGAs, IGBTs, ICs, and/or other similar devices known in the art allows the control module 1131 (or portions thereof) to be programmable and function according to certain logic rules and thresholds without the use of a hardware processor. Alternatively, FPGAs, IGBTs, ICs, and/or similar devices can be used in conjunction with one or more hardware processors 1188.

The transceiver 1179 of the control module 1131 can send and/or receive control and/or communication signals. Specifically, the transceiver 1179 can be used to transfer data between the control module 1131, the user 1190, and the network manager 1185. The transceiver 1179 can use wired and/or wireless technology. The transceiver 1179 can be configured in such a way that the control and/or communication signals sent and/or received by the transceiver 1179 can be received and/or sent by another transceiver that is part of the user 1190 and/or the network manager 1185.

When the transceiver 1179 uses wireless technology as the communication link 1122, any type of wireless technology can be used by the transceiver 1179 in sending and receiving signals. Such wireless technology can include, but is not limited to, Wi-Fi, visible light communication, cellular networking, and Bluetooth. The transceiver 1179 can use one or more of any number of suitable communication protocols (e.g., ISA100) when sending and/or receiving signals. Such communication protocols can be dictated by the communication module 1191. Further, any transceiver information for the user 1190 and/or the network manager 1185 can be stored in the storage repository 1160.

Optionally, in one or more example embodiments, the security module 1187 secures interactions between the control module 1131, the user 1190, and the network manager 1185. More specifically, the security module 1187 authenticates communication from software based on security keys verifying the identity of the source of the communication. For example, user software may be associated with a security key enabling the software of the user 1190 to interact with the control module 1131 and/or the network manager 1185. Further, the security module 1187 can restrict receipt of information, requests for information, and/or access to information in some example embodiments.

Figure 12:
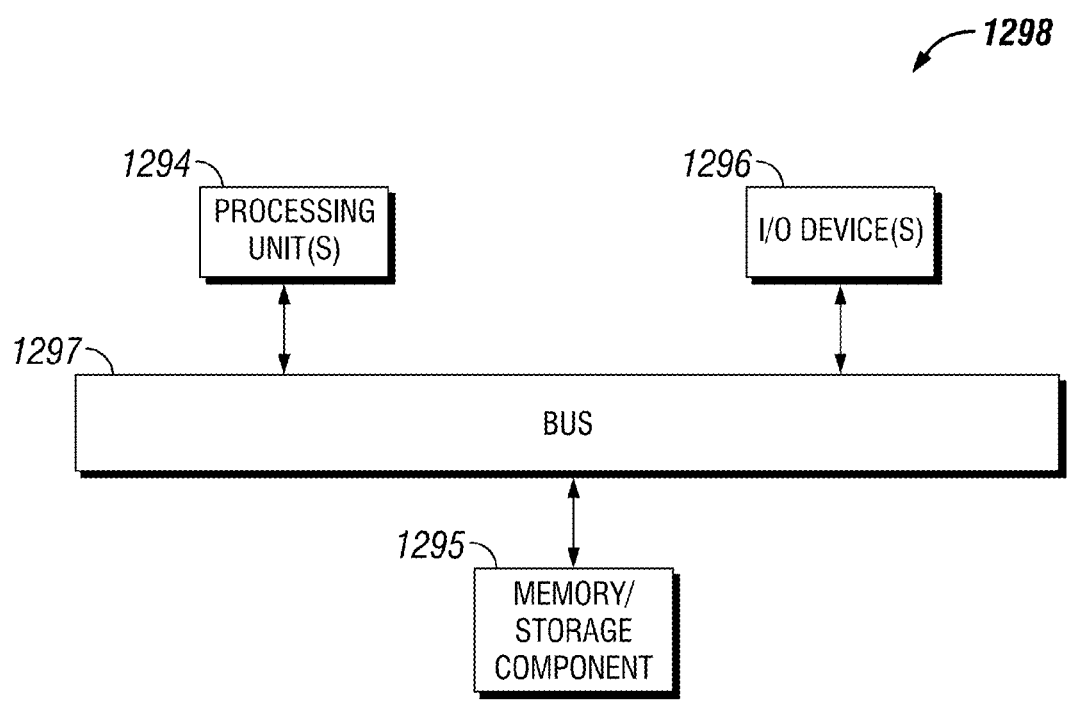
FIG. 12 shows a computing device in accordance with one or more example embodiments.

One or more of the functions performed by any of the components (e.g., control module 1131) of an example corrosion tracking system 1130 can be performed using a computing device 1298. An example of a computing device 1298 is shown in FIG. 12. The computing device 1298 implements one or more of the various techniques described herein, and which is representative, in whole or in part, of the elements described herein pursuant to certain example embodiments. Computing device 1298 is one example of a computing device and is not intended to suggest any limitation as to scope of use or functionality of the computing device and/or its possible architectures. Neither should computing device 1298 be interpreted as having any dependency or requirement relating to any one or combination of components illustrated in the example computing device 1298.

Computing device 1298 includes one or more processors or processing units 1294, one or more memory/storage components 1295, one or more input/output (I/O) devices 1296, and a bus 1297 that allows the various components and devices to communicate with one another. Bus 1297 represents one or more of any of several types of bus structures, including a memory bus or memory controller, a peripheral bus, an accelerated graphics port, and a processor or local bus using any of a variety of bus architectures. Bus 1297 includes wired and/or wireless buses.

Memory/storage component 1295 represents one or more computer storage media. Memory/storage component 1295 includes volatile media (such as random access memory (RAM)) and/or nonvolatile media (such as read only memory (ROM), flash memory, optical disks, magnetic disks, and so forth). Memory/storage component 1295 includes fixed media (e.g., RAM, ROM, a fixed hard drive, etc.) as well as removable media (e.g., a Flash memory drive, a removable hard drive, an optical disk, and so forth).

One or more I/O devices 1296 allow a customer, utility, or other user to enter commands and information to computing device 1298, and also allow information to be presented to the customer, utility, or other user and/or other components or devices. Examples of input devices include, but are not limited to, a keyboard, a cursor control device (e.g., a mouse), a microphone, and a scanner. Examples of output devices include, but are not limited to, a display device (e.g., a monitor or projector), speakers, a printer, and a network card.

Various techniques are described herein in the general context of software or program modules. Generally, software includes routines, programs, objects, components, data structures, and so forth that perform particular tasks or implement particular abstract data types. An implementation of these modules and techniques are stored on or transmitted across some form of computer readable media. Computer readable media is any available non-transitory medium or non-transitory media that is accessible by a computing device. By way of example, and not limitation, computer readable media includes "computer storage media".

"Computer storage media" and "computer readable medium" include volatile and non-volatile, removable and non-removable media implemented in any method or technology for storage of information such as computer readable instructions, data structures, program modules, or other data. Computer storage media include, but are not limited to, computer recordable media such as RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which is used to store the desired information and which is accessible by a computer.

The computer device 1298 is connected to a network (not shown) (e.g., a local area network (LAN), a wide area network (WAN) such as the Internet, or any other similar type of network) via a network interface connection (not shown) according to some example embodiments. Those skilled in the art will appreciate that many different types of computer systems exist (e.g., desktop computer, a laptop computer, a personal media device, a mobile device, such as a cell phone or personal digital assistant, or any other computing system capable of executing computer readable instructions), and the aforementioned input and output means take other forms, now known or later developed, in other example embodiments. Generally speaking, the computer system 1298 includes at least the minimal processing, input, and/or output means necessary to practice one or more embodiments.

Further, those skilled in the art will appreciate that one or more elements of the aforementioned computer device 1298 is located at a remote location and connected to the other elements over a network in certain example embodiments. Further, one or more embodiments is implemented on a distributed system having one or more nodes, where each portion of the implementation (e.g., control module 1131) is located on a different node within the distributed system. In one or more embodiments, the node corresponds to a computer system. Alternatively, the node corresponds to a processor with associated physical memory in some example embodiments. The node alternatively corresponds to a processor with shared memory and/or resources in some example embodiments.

Example embodiments can provide for detecting and monitoring corrosion within electrical enclosures and/or other environments. Specifically, certain example embodiments can use an electrical circuit. When current flows through the electrical circuit, a magnetic field is generated and emanates from the electrical circuit. By placing a target component proximate to the electrical circuit, the magnetic field can induce eddy currents in the target component. The target component in example embodiments is subject to corrosion that may exist in the volume of space proximate to where example corrosion tracking systems are placed. A sensor can be used to measure the flow of eddy currents in the target component. By tracking the flow of eddy currents in the target component over time, example embodiments can indicate an extent of corrosion that may exist in the volume of space proximate to where example corrosion tracking systems are placed.

Although embodiments described herein are made with reference to example embodiments, it should be appreciated by those skilled in the art that various modifications are well within the scope and spirit of this disclosure. Those skilled in the art will appreciate that the example embodiments described herein are not limited to any specifically discussed application and that the embodiments described herein are illustrative and not restrictive. From the description of the example embodiments, equivalents of the elements shown therein will suggest themselves to those skilled in the art, and ways of constructing other embodiments using the present disclosure will suggest themselves to practitioners of the art. Therefore, the scope of the example embodiments is not limited herein.

What is claimed is:

1. A corrosion tracking system within an electrical enclosure, the system comprising:
   an electrical circuit having a spiral-wound shape when viewed from above and through which a first current flows, wherein the first current creates a magnetic field;
   a first sacrificial loop disposed above or below the electrical circuit, wherein the magnetic field induces a plurality of second currents to flow within the first sacrificial loop; and
   a sensor that measures the plurality of second currents flowing within the first sacrificial loop to generate a plurality of measurements,
   wherein the plurality of measurements indicates whether the first sacrificial loop is experiencing corrosion,
   wherein the electrical circuit, the first sacrificial loop, and the sensor are located within a cavity of the electrical enclosure.

2. The system of claim 1, wherein the first sacrificial loop comprises a known material, has a known shape and size, and is located a distance from the electrical circuit.

3. The system of claim 1, further comprising a second sacrificial loop disposed proximate to the electrical circuit and the sensor.

4. The system of claim 3, wherein a third sacrificial loop is disposed proximate to an additional electrical circuit of a plurality of electrical circuits and an additional sensor of a plurality of sensors.

5. The system of claim 1, wherein the electrical circuit and the sensor are part of a same device.

6. The system of claim 1, wherein the electrical circuit and the sensor comprise a non-corrosive material.

7. The system of claim 1, wherein the electrical circuit and the sensor are hermetically sealed.

8. The system of claim 1, wherein the corrosion of the first sacrificial loop is non-uniform throughout the first sacrificial loop.

9. The system of claim 1, wherein the first sacrificial loop is a loop coupon.

10. The system of claim 1, wherein the first sacrificial loop is stationary relative to the electrical circuit and the sensor.

11. The system of claim 1, wherein the plurality of measurements are taken over time and indicates that the corrosion of the first sacrificial loop is becoming more extensive.

12. The system of claim 1, wherein the plurality of second currents are eddy currents.

13. The system of claim 1, further comprising:
   a controller coupled to the sensor, wherein the controller tracks the plurality of measurements, applies the plurality of measurements to at least one algorithm to determine whether the first sacrificial loop is experiencing corrosion, and communicates the corrosion of the first sacrificial loop to a user.

14. The system of claim 13, wherein the controller is further coupled to the electrical circuit, wherein the controller controls the first current flowing through the electrical circuit.

15. The system of claim 1, wherein the electrical circuit is an inductor.

16. The system of claim 1, wherein the first sacrificial loop is untreated to allow for natural corrosion.

17. An electrical enclosure comprising:
   at least one wall that forms a cavity;
   a first device disposed within the cavity, wherein the first device comprises a first material subject to first corrosion;
   a first corrosion tracking system disposed within the cavity adjacent to the first device, wherein the first corrosion tracking system comprises:
      a first electrical circuit having a spiral-wound shape when viewed from above and through which a first current flows, wherein the first current creates a first magnetic field;
      a first sacrificial loop disposed above or below the first electrical circuit, wherein the first magnetic field induces a plurality of second currents to flow within the first sacrificial loop; and
      a first sensor that measures the plurality of second currents flowing within the first sacrificial loop to generate a plurality of first measurements,
   wherein the plurality of first measurements indicates whether the first sacrificial loop is experiencing second corrosion, and
   wherein the second corrosion of the first sacrificial loop indicates a level of the first corrosion in the first device.

18. The electrical enclosure of claim 17, further comprising:
   a controller coupled to the first sensor, wherein the controller tracks the plurality of first measurements, determines, using the plurality of first measurements, whether the first sacrificial loop is experiencing the second corrosion, and communicates the second corrosion of the first sacrificial loop to a user.

19. The electrical enclosure of claim 17, comprising:
   a second device disposed within the cavity, wherein the second device comprises a second material subject to third corrosion;
   a second corrosion tracking system disposed within the cavity adjacent to the second device, wherein the second corrosion tracking system comprises:
      a second electrical circuit through which a third current flows, wherein the third current creates a second magnetic field;
      a second sacrificial loop disposed proximate to the second electrical circuit, wherein the second magnetic field induces a plurality of fourth currents to flow within the second sacrificial loop; and
      a second sensor that measures the plurality of fourth currents flowing within the second sacrificial loop to generate a plurality of second measurements, wherein the plurality of second measurements indicates whether the second sacrificial loop is experiencing fourth corrosion, and wherein the fourth corrosion of the second sacrificial loop indicates a level of the third corrosion in the second device.

\* \* \* \* \*